United States Patent [19]
Dedo

[11] Patent Number: 4,705,025
[45] Date of Patent: Nov. 10, 1987

[54] HEEL PADDING

[76] Inventor: Richard G. Dedo, 175 Denise Dr., Hillsborough, Calif. 94010

[21] Appl. No.: 876,780

[22] Filed: Jun. 20, 1986

[51] Int. Cl.[4] .......................... A61F 5/30; A61F 5/14; A61B 19/00
[52] U.S. Cl. .................................... 128/153; 128/149; 128/581
[58] Field of Search .................. 128/80 R, 80 H, 165, 128/89 R, 681, 166, 166.5, 91 R, 149, 153; 36/92, 71, 80

[56] References Cited

U.S. PATENT DOCUMENTS

| | | | |
|---|---|---|---|
| 3,508,544 | 4/1970 | Moore et al. | 128/149 |
| 3,584,622 | 6/1971 | Domenico | 128/166 |
| 3,937,218 | 2/1976 | Gaylord, Jr. | 128/149 |
| 4,479,490 | 10/1984 | Dedo | 128/89 R |

FOREIGN PATENT DOCUMENTS 0474960  4/1929  Fed. Rep. of Germany ....... 36/58.5

Primary Examiner—Robert A. Hafer
Assistant Examiner—Kathleen D'Arrigo
Attorney, Agent, or Firm—Powell L. Sprunger

[57] ABSTRACT

A heel pad comprising, a sheet of porous material having a hemispherical portion for placement on the heel, first and second opposed flap portions extending upwardly from the hemispherical portion and a central portion connecting the first and second flap portions. The pad has third and fourth flap opposed flap portions extending downwardly from the hemispherical portion, and a central portion connecting the third and fourth flap portions. The third and fourth flap portions are adapted to overlap upper portions over lower portions of the first and second flap portions, with the first and second flap portions facing each other, and with the third and fourth flap portions facing each other in the formed sheet.

14 Claims, 15 Drawing Figures

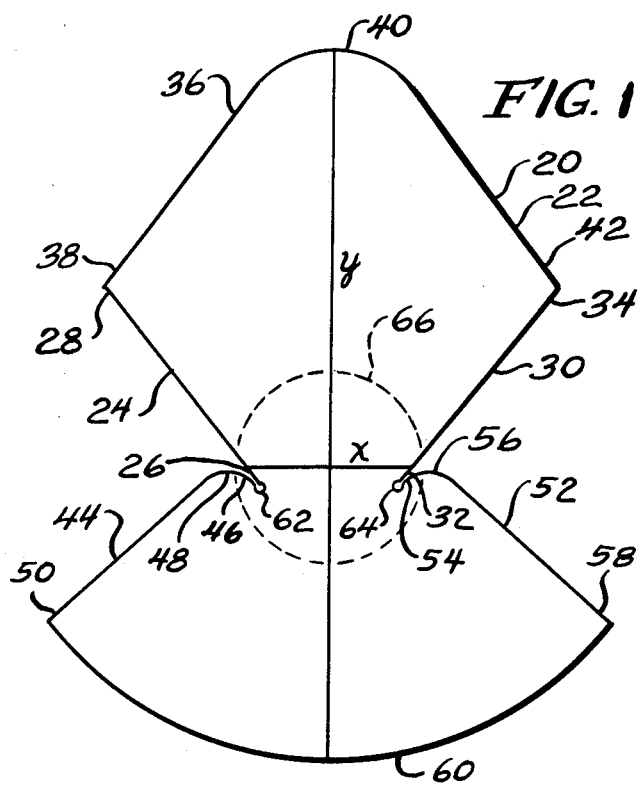
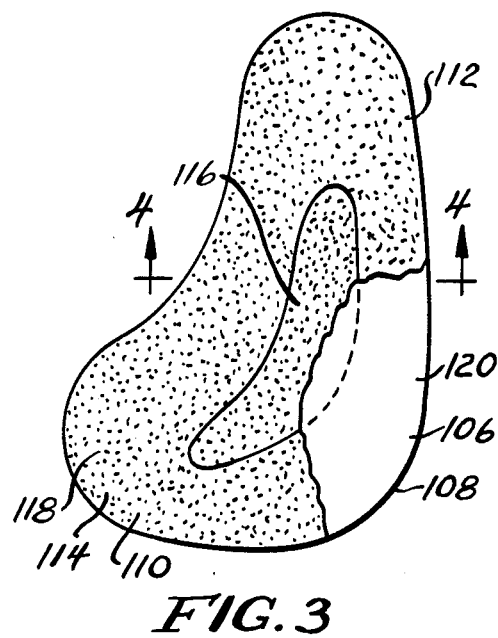
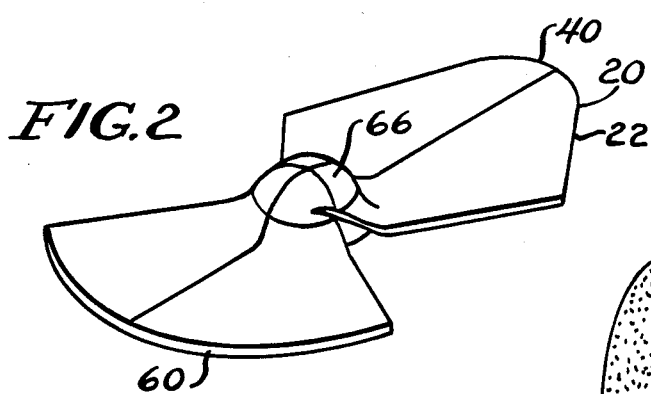
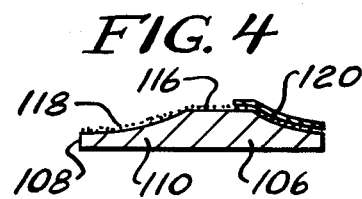
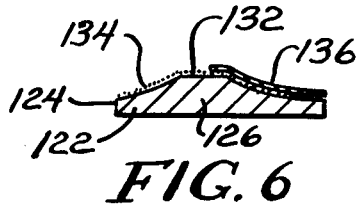
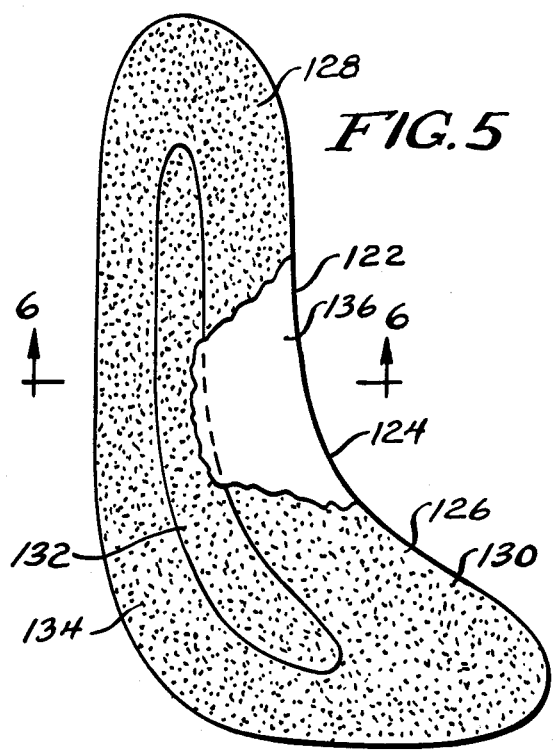

HEEL PADDING

BACKGROUND OF THE INVENTION

The present invention relates to padding for the lower extremity.

A heel pad is disclosed in FIG. 10 of U.S. Pat. No. 4,479,490, invented by the present applicant. Although the heel pad operates satisfactorily in covering the heel to facilitate wrapping of wadding around the heel, such that it is not necessary to wrap the wadding thick in front and thin in back due to the radius of the ankle, it is desirable to provide a heel padding which is adjustable to various sizes of the foot in order to eliminate inventory of the heel pads for different sizes of feet.

A case should adapt closely to the extremity being immobilized to eliminate motion, and allow bones and/or ligaments to heal. The two bony prominences at the ankle are the fibular malleolus laterally and the tibial malleolus medially. they are covered laterally and medially, and both are covered posteriorly, only by a thin layer of subcutaenous fat and skin. Therefore, they should be well padded. Presently, the area is wrapped circumferentially with sheet wadding, and then a cast is formed around the malleoli. The depressions behind the malleoli swell as the result of distal leg, ankle, or foot trauma, and when the swelling subsides, the cast loosens. It is desirable to solve this problem.

SUMMARY OF THE INVENTION

A principal feature of the present invention is the provision of an improved heel pad for forming a cast.

The heed pad of the present invention comprises, a sheet of porous material having a hemispherical portion, first and second opposed flap portions extending upwardly from the hemispherical portion and a central portion connecting the first and second flap portions. The pad has third and fourth opposed flap portions extending downwardly from the hemispherical portion, and a central portion connecting the third and fourth flap portions. The first and second flap portions face each other, and the third and fourth flap portions face each other in the formed sheet.

A feature of the present invention is that the hemispherical portion is adapted for placement on the heel.

Another feature of the invention is that the third and fourth flap portions are adapted to overlap upper portions over lower portions of the first and second flap portions.

A feature of the present invention is that the upper first and second flap portions and central portion are adapted to cover the area of the achilles' tendon and heel.

Yet another feature of the invention is that the lower third and fourth flap portions are adapted to cover the lower part of the foot and heel.

Another feature of the invention is that the third and fourth flap portions may overlap the first and second flap portions to a desired extent in order to provide adjustment of the heel pad to the size of the foot, or to accommodate varying degrees of equinus.

Thus, a feature of the present invention is that the heel pad eliminates the necessity of maintaining an inventory of various size heel pads for different sized feet.

A feature of the present invention is that the heel pad facilitates wrapping of sheet wadding which normally results in wrapped wadding very thick in front of the ankle and very thin in back of the heel.

A further feature of the present invention is the provision of medial and lateral malleoli pads for placement behind and below the malleoli, after which the heel pad is located over the malleoli pads.

Thus, a feature of the present invention is that the normal depressions behind the malleoli are at least partially filled by the two pads, and also pad the posterior aspect of the two subcutaneous surfaces of the malleoli.

Accordingly, a feature of the present invention is that the heel and malleoli pads provide coverage for the medial aspect of the tibial malleolus, and the lateral aspect of the lateral malleolus, and the heel.

Further features will become more fully apparent in the following description of the embodiments of this invention and from the appended claims.

DESCRIPTION OF THE DRAWINGS

In the drawings:

FIG. 1 is a plan view of a porous sheet cut to form a heel pad of the present invention;

FIG. 2 is a perspective view of a partially formed heel pad by the sheet of FIG. 1;

FIG. 3 is an elevational view of a medial malleolus pad;

FIG. 4 is a sectional view taken substantially as indicated along the line 4—4 of FIG. 3;

FIG. 5 is an elevational view of a lateral malleolus pad;

FIG. 6 is a sectional view taken substantially as indicated along the line 6—6 of FIG. 5;

DESCRIPTION OF THE PREFERRED EMBODIMENTS

Figure 7:
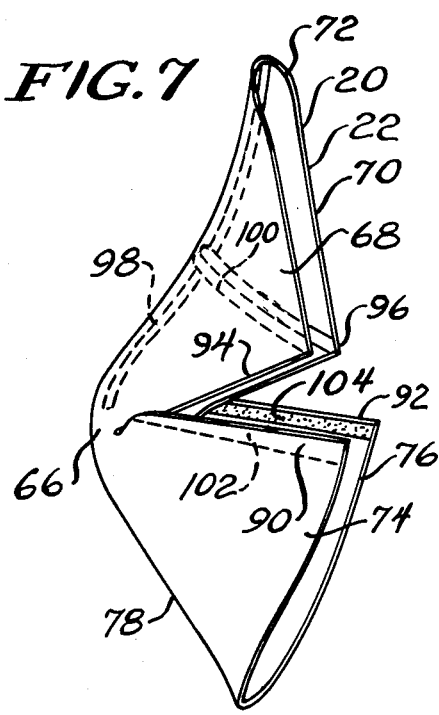
FIG. 7 is a perspective view of a heel pad further formed from the configuration of FIG. 2.

Referring now to FIG. 1, there is shown a sheet 20 of porous material, such as felt, which is cut into a configuration to form a heel pad 22 of the present invention. The heel pad 22 of FIG. 1 will be discussed with reference to orthogonal x and y axes, as shown. The sheet 20 is porous in order to permit the heel pad to breathe during use of the pad 22 on a patient's foot.

The sheet 20 has a first generally straight side edge 24 spaced from the juncture of the x and y axes and having a first end 26 located slightly below the x axis on one side of the y axis. The first side edge 24 extends upwardly along the y axis and away from the y axis at an acute angle to the y axis and terminates at a second end 28 substantially above the x axis. The sheet 20 has a second generally straight side edge 30 spaced from the juncture of the x and y axes and having a first end 32 located slightly below the x axis on the other side of the y axis. The second side edge 30 extends upwardly along the y axis and away from the y axis at an acute angle to the y axis and terminates at a second end 34 substantially above the x axis at approximately the y coordinate of the second end 28 of the first side edge 24. The sheet 20 has a third side edge 36 having a first end 38 extending from the second end 28 of the first side edge 24 in a generally straight line upwardly along the toward the y axis to an arcuate portion 40 crossing the y axis. The third side edge 36 has a second end 42 extending from the second end 34 of the second side edge 30 in a generally straight line upwardly along and toward the y axis to the arcuate portion 40.

The sheet 20 has a fourth side edge 44 having a first end 46 extending from the first end 26 of the first side edge 24 in an arcuate portion 48 located adjacent the x axis and extending in a generally straight line downwardly from the x axis and directed outwardly from the y axis and terminating in a second end 50. The sheet 20 has a fifth side edge 52 having a first end 54 extending from the first end 32 of the second side edge 30 in an arcuate portion 56 located adjacent the x axis and extending in a generally straight line downwardly from the x axis and directed outwardly from the y axis and terminating in a second end 58. The sheet 20 also has an arcuate sixth side edge 60 connecting the second ends 50 and 58 of the fourth and fifth side edges 44 and 52 and crossing the y axis. The sheet 20 has relatively small circular cut-outs 62 and 64 at the juncture of the first ends 26 and 46 of the first and fourth side edges 24 and 44 and also the first ends 32 and 54 of the second and fifth side edges 30 and 52.

The sheet 20 has a hemispherical portion 66 indicated in dotted lines centered at the juncture of the x and y axes. The hemispherical portion 66 extends past the juncture of the first and fourth side edges 24 and 44 and the juncture of the second and fifth side edges 30 and 52.

With reference to FIG. 2, a male and female mold is utilized to stretch the felt sheet 20 to form the hemispherical portion 66 which is raised from the remainder of the plane of the sheet 20. As will be seen below, the curved hemispherical portion 66 is utilized for placement on the patient's heel.

Figure 8:
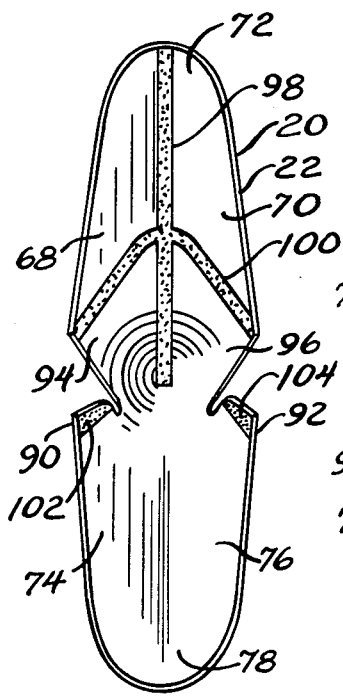
FIG. 8 is a front elevational view of the heel pad of FIG. 7.
Figure 9:
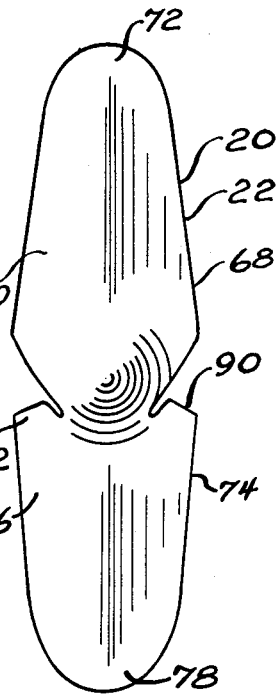
FIG. 9 is a rear elevational view of the heel pad of FIG. 7.

With reference to FIGS. 7-9, the sheet 20 of FIG. 1 is formed into curved configurations which will be described below. The sheet 20 forming the heel pad 22 of FIGS. 7-9 has the hemispherical portion 66 for placement on the heel, first and second opposed flap portions 68 and 70 extending upwardly from the hemispherical portion 66, and a central portion 72 connecting the first and second flap portions 68 and 70. The formed sheet 20 of the heel pad 22 has third and fourth opposed flap portions 74 and 76 extending downwadly from the hemispherical portion 66, and a central portion 78 connecting the third and fourth flap portions 74 and 76. As will be seen below, the third and fourth flap portions 74 and 76 have upper portions 90 and 92 which are adapted to overlap lower portions 94 and 96 of the first and second flap portions 68 and 70. In the formed configuration of sheet 20, the first and second flap portions 68 and 70 face each other in the formed sheet 20, and the third and fourth flap portions 74 and 76 face each other in the formed sheet 20. As previously described in connection with FIG. 1, the third and fourth flap portions 74 and 76 have side edges defining upper arcuate portions in the region of the hemispherical portion 66. Also, as previously described in connection with FIG. 1, the first and second flap portions 68 and 70 have generally straight edges extending outwardly from the hemispherical portion 66.

With reference to FIGS. 1, 7, and 8, the sheet 20 has a line of adhesive 98 on an inner surface of the sheet 20 and extending from the juncture of the x and y axes upwardly along the y axis. The sheet 20 also has a line of adhesive 100 on an inner surface of the sheet 20 and extending between the second ends 28 and 34 of the first and second side edges 24 and 30 across the y axis. Further, the sheet 20 has lines of adhesive 102 and 104 on an inner surface of the sheet 20 extending substantially the length of and along the fourth and fifth side edges 44 and 52. Stated with respect to FIG. 7-9, the sheet 20 has lines of adhesive 102 and 104 on an inner surface of the sheet 20 and along upper side edges of the third and fourth flap portions 74 and 76 which may overlap the first and second flap portions 68 and 70. The sheet 20 has a line of adhesive 98 on an inner surface of the sheet 20 and extending along the central portion 72 between the first and second flap portions 68 and 70. The sheet 20 also has a line of adhesive 100 on an inner surface of the sheet 20 and extending across the first and second flap portions 68 and 70 and the central portion 72.

With reference to FIGS. 3 and 4, there is shown a medial malleolus pad 106 having side edges 108 forming the pad 106 into a generally arcuate configuration. The pad 106 comprises a sheet 100 of porous material, such as felt, to permit breathing during use, having an upper arcuate portion 112 for placement behind the malleolus, and a lower arcuate portion 114 extending to one side of the upper arcuate portion 112 for placement below the malleolus. The sheet 110 is tapered, such as by skiving, from an elongated raised central portion 116 toward the side edges 108 of the sheet 110. The pad 106 has an adhesive 118 covering the tapered surface of the sheet 110. The pad 106 has a release sheet 120 releasably covering the adhesive 118 in order to protect the adhesive 118 prior to use.

With reference to FIGS. 5 and 6, there is shown a lateral malleolus pad 122 having side edges 124 forming a generally arcuate configuration of the pad 122. The pad 122 comprises a sheet 126 of porous material, such as felt, to permit breathing of the pad 122 during use. The sheet 126 has an upper arcuate portion 128 for placement behind the malleolus, and a lower arcuate portion 130 extending to one side of the upper portion 128 for placement below the malleolus. The sheet 126 is tapered, such as by skiving, from an elongated raised central portion 132 toward the side edges 124 of the sheet 126. The pad 122 has an adhesive 134 covering the tapered surface of the pad 122, and a release sheet 136 releasably covering the adhesive 134 to protect the adhesive 134 prior to use.

Figure 10:
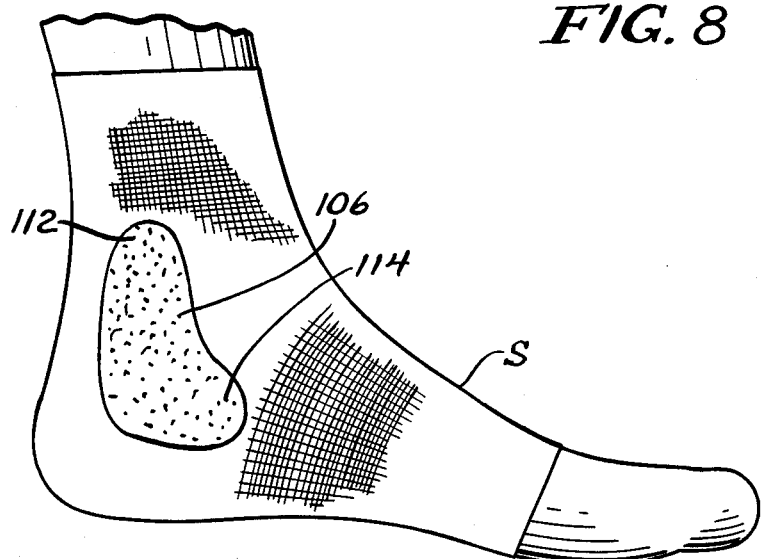
FIG. 10 is an elevational view of a foot illustrating placement of the medial malleolus pad.
Figure 11:
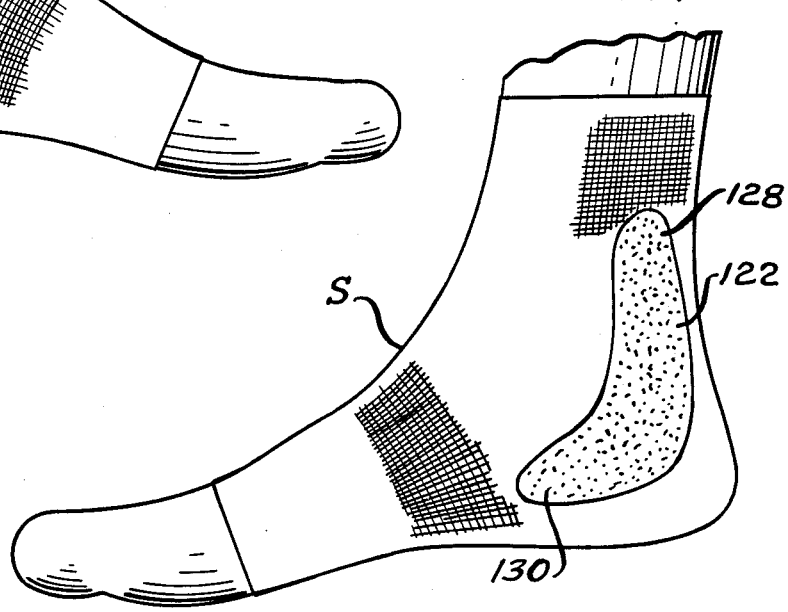
FIG. 11 is an elevational view of the foot showing placement of the lateral malleolus pad.
Figure 12:
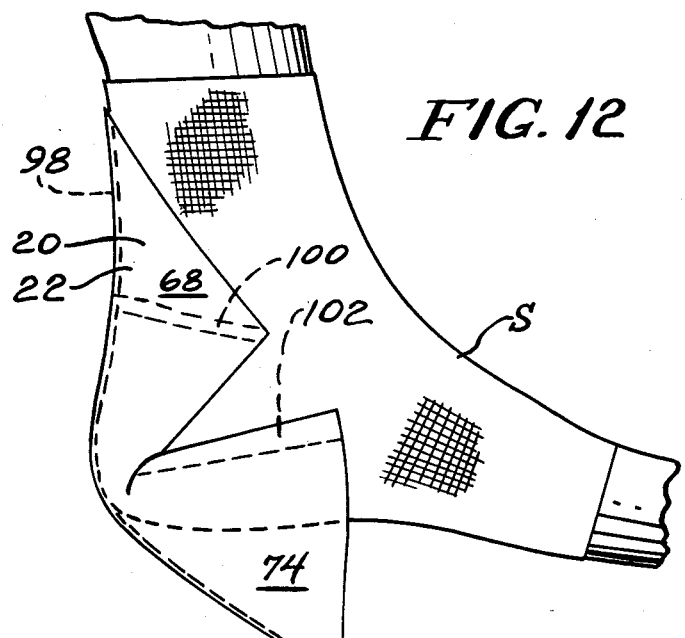
FIG. 12 is an elevational view showing partial placement of the heel pad on a patient's foot.
Figure 13:
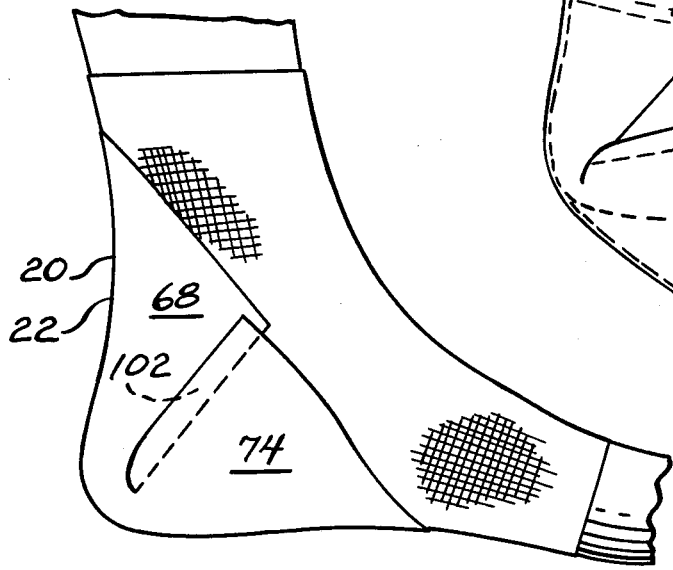
FIG. 13 is an elevational view showing placement of the heel pad on the patient's foot.
Figure 14:
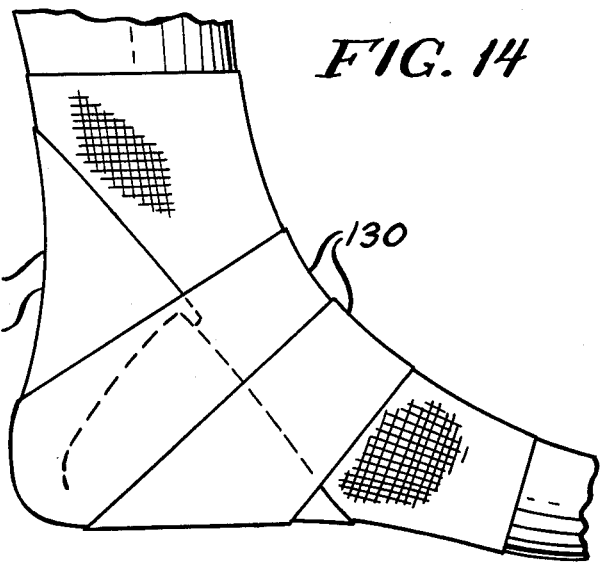
FIG. 14 is an elevational view showing partial wrapping of a wadding sheet over the heel pad and ankle of the patient.
Figure 15:
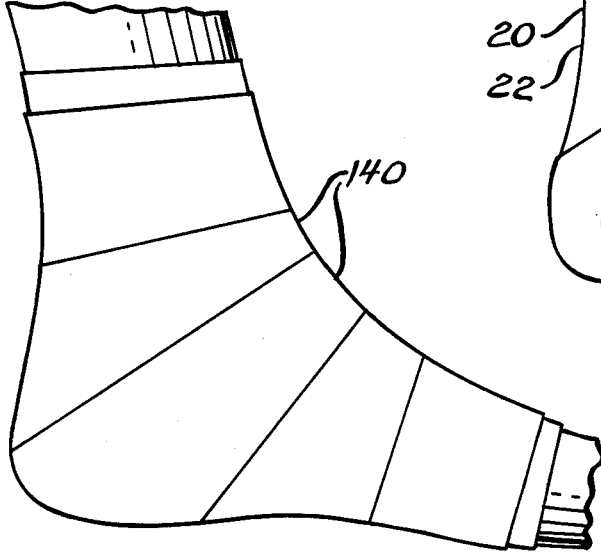
FIG. 15 is an elevational view illustrating a wrapped cast over the sheet wadding of FIG. 14.

In use, a tubular stockinette material of known type is placed over the foot, as shown in FIGS. 10 and 11, such that it at least covers the ankle, heel, and instep of the foot. Next, the release sheets are removed from the malleoli pads 106 and 122, and the adhesive on the pads 106 and 122 is utilized to secure the pads in place on the stockinette material behind and below the malleoli. Next, with reference to FIG. 12, the upper part of the heel pad 22 comprising the first and second flap portions 68 and 70 and central portion 72 are applied to the upper part of the back of the leg over the achilles tendon and heel, and the flap portions 68 and 70 are brought forward and around the posterior part of the heel, and are adhered to the pads 106 and 122 and stockinette material by the adhesive lines 98 and 100. Next, the third and fourth flap portions 74 and 76 are brought under both sides of the bottom of the heel, and are adhered to the upper flap portions 68 and 70 already in place by the adhesive lines 102 and 104, as shown in FIG. 13. In this regard, it will be noted that the lower third and fourth flap portions 74 and 76 may be brought upwardly over the first and second flap portions 68 and 70 to a desired extent in order to comfortably fit the heel, such that the heel pad 22 is adjustable to different sized feet. Next, with reference to FIG. 14, a sheet wadding 138 of known type is wrapped over the foot, heel, and ankle in order to cover the pads and stockinette material in this region. In this regard, it should be noted that the radius of the adult ankle is about three inches in front, and nine inches in back. Normally, when the sheet wadding is wrapped it becomes very thick in front, and very thin in back. However, due to the heel padding 22 of the present invention the wadding need not be wrapped with this variation of thickness in front and back due to the heel pad 22. After the foot has been wrapped by the sheet wadding 138, the area covered by the sheet wadding 138 is wrapped by an elongated sheet of plaster 140 which hardens in order to complete the cast.

In accordance with a method of forming a cast on a lower extremity of a patient according to the present invention, the following steps are performed. A stockinette material is placed over the distal portion of the leg and foot, a pad is placed behind and below the lateral malleolus, a pad is placed behind and below the medial malleolus, a pad is placed over the heel, and the foot and distal leg are wrapped with sheet wadding over the pads, and a cast is formed over the wrapped sheet wadding.

The foregoing detailed description is given for clearness of understanding only, and no unnecessary limitations should be understood therefrom, as modifications will be obvious to those skilled in the art.

I claim:

1. A heel pad as formed with regard to orthogonal x and y axes, comprising:
   a sheet of porous material having a first generally straight side edge spaced from the juncture of the x and y axes and having a first end located slightly below the x axis on one side of the y axis, said first side edge extending upwardly along the y axis and away from the y axis at an acute angle to the y axis and terminating at a second end substantially above the x axis, a second generally straight side edge spaced from the juncture of the x and y axes and having a first end located slightly below the x axis on the other side of the y axis, said second side edge extending upwardly along the y axis and away from the y axis at an acute angle to the y axis and terminating at a second end substantially above the x axis at approximately the y coordinate of the second end of the first side edge, a third side edge having a first end extending from the second end of the first side edge in a generally straight line upwardly along and toward the y axis to an arcuate portion crossing the y axis, and a second end extending from the second end of the second side edge in a generally straight line upwardly along and toward the y axis to said arcuate portion, a fourth side edge having a first end extending from the first end of the first side edge in an arcuate portion located above the first ends of the first and fourth side edges adjacent the x axis and extending in a generally straight line downwardly from the x axis and directed outwardly from the y axis and terminating in a second end, a fifth side edge having a first end extending from the first end of the second side edge in an arcuate portion located above the first ends of the second and fifth side edges adjacent the x axis and extending in a generally straight line downwardly from the x axis and directed outwardly from the y axis and terminating in a second end, and an arcuate sixth side edge connecting the second ends of the fourth and fifth side edges and crossing the y axis.

2. The pad of claim 1 wherein the sheet has relatively small circular cut-outs at the juncture of the first ends of the first and fourth side edges and the first ends of the second and fifth side edges.

3. The pad at claim 1 wherein the sheet has a hemispherical portion centered at the juncture at the x and y axes.

4. The pad of claim 3 wherein the hemispherical portion extends past the juncture of the first and fourth side edges and the juncture of the second and fifth side edges.

5. The pad of claim 1 including a line of adhesive on an inner side of the sheet and extending from the juncture of the x and y axis upwardly along the y axis.

6. The pad of claim 1 including a line of adhesive on an inner side of the sheet and extending between the second ends of the first and second side edges across the y axis.

7. The pad of claim 1 including lines of adhesive on an inner side of the sheet extending substantially the length of and along the fourth and fifth side edges.

8. A heel pad, comprising:
   a sheet of porous material having a hemispherical portion for placement on the heel, first and second opposed flap portions extending upwardly from the hemispherical portion and a central portion connecting the first and second flap portions, third and fourth opposed flap portions extending downwardly from the hemispherical portion, and a central portion connecting the third and fourth flap portions, said third and fourth flap portions being adapted to overlap upper portions over lower portions of the first and second flap portions, with the first and second flap portions facing each other and with the third and fourth flap portions facing each other in the formed sheet.

9. The pad of claim 8 wherein the third and fourth flap portions having side edges defining upper arcuate portions in the region of the hemispherical portion.

10. The pad of claim 9 wherein the first and second flap portions have generally straight side edges extending outwardly from the hemispherical portion.

11. The pad of claim 8 including lines of adhesive on an inner surface of the sheet and along upper side edges of the third and fourth flap portions which may overlap the first and second flap portions.

12. The pad of claim 8 including a line of adhesive on an inner surface of the sheet and extending along the central portion between the first and second flap portions.

13. The pad of claim 8 including a line of adhesive on an inner surface of the sheet and extending across the first and second flap portions and the central portion therebetween.

14. The pad of claim 8 including a small circular cutout at the juncture of the first and third flap portions and the juncture of the second and fourth flap portions.

* * * * *